(12) United States Patent
Farnan

(10) Patent No.: US 7,691,119 B2
(45) Date of Patent: Apr. 6, 2010

(54) BALLOON CATHETER WITH NON-DEPLOYABLE STENT

(75) Inventor: Robert C. Farnan, Davie, FL (US)

(73) Assignee: AngioScore, Inc., Fremont, CA (US)

( * ) Notice: Subject to any disclaimer, the term of this patent is extended or adjusted under 35 U.S.C. 154(b) by 759 days.

(21) Appl. No.: 10/399,589

(22) PCT Filed: Nov. 6, 2002

(86) PCT No.: PCT/US02/35547

§ 371 (c)(1),
(2), (4) Date: Sep. 2, 2003

(87) PCT Pub. No.: WO03/041760

PCT Pub. Date: May 22, 2003

(65) Prior Publication Data

US 2005/0049677 A1    Mar. 3, 2005

(51) Int. Cl.
*A61B 17/22* (2006.01)
*A61M 29/00* (2006.01)

(52) U.S. Cl. .................. 606/194; 606/191; 606/159

(58) Field of Classification Search .......... 606/191, 606/194, 159; 623/1.23; 604/103.07, 103.08
See application file for complete search history.

(56) References Cited

U.S. PATENT DOCUMENTS

| | | | |
|---|---|---|---|
| 2,854,983 A | 10/1958 | Baskin | |
| 4,950,227 A | 8/1990 | Savin et al. | |
| 5,071,407 A | 12/1991 | Termin et al. | |
| 5,102,417 A | 4/1992 | Palmaz | |
| 5,108,416 A | 4/1992 | Ryan et al. | |
| 5,176,693 A * | 1/1993 | Pannek, Jr. ............. | 606/159 |
| 5,190,058 A | 3/1993 | Jones et al. | |
| 5,449,373 A | 9/1995 | Pinchasik et al. | |
| 5,456,667 A | 10/1995 | Ham et al. | |
| 5,527,282 A | 6/1996 | Segal | |

(Continued)

FOREIGN PATENT DOCUMENTS

EP    1 179 323 A2    2/2002

(Continued)

OTHER PUBLICATIONS

PCT Search Report mailed May 20, 2003 by Jacki Tan-Uyen T. Ho.

(Continued)

*Primary Examiner*—Julian W Woo
*Assistant Examiner*—Melissa Ryckman
(74) *Attorney, Agent, or Firm*—Townsend and Townsend and Crew LLP

(57) ABSTRACT

An angioplasty balloon including a non-deployable stent to prevent or reduce the potential for slippage of the inflated balloon with respect to the vessel wall being treated. The balloon includes a non-deployable stent that is adapted to be secured to the balloon or angioplasty balloon catheter. The stent has a proximal end, a distal end, and at least three radially-spaced struts, each strut connecting the proximal end to the distal end and having one or more bends that allow expansion of the strut to accommodate the inflation of the balloon. The stent is made of a material so that the stent collapses upon deflation or the balloon.

9 Claims, 11 Drawing Sheets

U.S. PATENT DOCUMENTS

| | | | |
|---|---|---|---|
| 5,571,086 A | | 11/1996 | Kaplan et al. |
| 5,607,442 A | * | 3/1997 | Fischell et al. .............. 623/1.18 |
| 5,730,698 A | | 3/1998 | Fischell et al. |
| 5,755,781 A | | 5/1998 | Jayaraman |
| 5,766,238 A | | 6/1998 | Lau et al. |
| 5,797,935 A | * | 8/1998 | Barath ........................ 606/159 |
| 5,868,779 A | | 2/1999 | Ruiz |
| 5,904,698 A | | 5/1999 | Thomas et al. |
| 5,994,667 A | | 11/1999 | Merdan et al. ......... 219/121.67 |
| 6,036,686 A | | 3/2000 | Griswold |
| 6,036,689 A | | 3/2000 | Tu et al. |
| 6,053,913 A | * | 4/2000 | Tu et al. ....................... 606/41 |
| 6,071,285 A | | 6/2000 | Lashinski et al. |
| 6,071,286 A | | 6/2000 | Mawad |
| 6,077,298 A | | 6/2000 | Tu et al. |
| 6,106,548 A | * | 8/2000 | Roubin et al. ............... 623/1.15 |
| 6,117,104 A | | 9/2000 | Fitz |
| 6,146,323 A | | 11/2000 | Fischell |
| 6,152,944 A | | 11/2000 | Holman et al. |
| 6,190,403 B1 | | 2/2001 | Fischell et al. |
| 6,203,569 B1 | | 3/2001 | Wijay |
| 6,206,910 B1 | * | 3/2001 | Berry et al. ................. 623/1.15 |
| 6,309,414 B1 | | 10/2001 | Rolando et al. |
| 6,312,459 B1 | | 11/2001 | Huang et al. ................ 623/1.15 |
| 6,325,779 B1 | | 12/2001 | Zedler |
| 6,371,961 B1 | | 4/2002 | Osborne et al. |
| 6,416,539 B1 | | 7/2002 | Hassdenteufel |
| 6,475,234 B1 | | 11/2002 | Richter et al. |
| 6,569,180 B1 | | 5/2003 | Sirhan et al. |
| 6,605,107 B1 | | 8/2003 | Klein |
| 6,613,072 B2 | | 9/2003 | Lau et al. |
| 6,648,912 B2 | | 11/2003 | Trout, III et al. |
| 6,663,660 B2 | | 12/2003 | Dusbabek et al. |
| 2001/0001823 A1 | | 5/2001 | Ryan |
| 2001/0007082 A1 | | 7/2001 | Dusbabek et al. |
| 2001/0016753 A1 | | 8/2001 | Caprio et al. |
| 2002/0038144 A1 | | 3/2002 | Trout, III et al. |
| 2002/0045930 A1 | | 4/2002 | Burg et al. |
| 2002/0111633 A1 | | 8/2002 | Stoltze et al. |
| 2002/0165599 A1 | | 11/2002 | Nasralla |
| 2003/0028235 A1 | | 2/2003 | McIntosh et al. |
| 2003/0074046 A1 | | 4/2003 | Richter |
| 2003/0105509 A1 | | 6/2003 | Jang et al. |
| 2003/0149468 A1 | | 8/2003 | Wallsten |
| 2003/0171799 A1 | | 9/2003 | Lee et al. |
| 2003/0187494 A1 | | 10/2003 | Loaldi |
| 2003/0195609 A1 | | 10/2003 | Berenstein et al. |
| 2003/0199970 A1 | | 10/2003 | Shanley |
| 2003/0199988 A1 | | 10/2003 | Devonec et al. |
| 2003/0208255 A1 | | 11/2003 | O'Shaughnessy et al. |
| 2006/0149308 A1 | | 7/2006 | Melsheimer et al. |
| 2006/0184191 A1 | | 8/2006 | O'Brien |

FOREIGN PATENT DOCUMENTS

| | | |
|---|---|---|
| WO | WO 98/05377 | 2/1998 |
| WO | WO 03/041760 A2 | 5/2003 |

OTHER PUBLICATIONS

PCT Search Report for International Application No. PCT/US04/27836, mailed Dec. 30, 2004 by Jackie Tan-Uyen T. Ho.

* cited by examiner

BALLOON CATHETER WITH NON-DEPLOYABLE STENT

BACKGROUND OF THE INVENTION

When a balloon used for percutaneous transluminal angioplasty (PTA) or percutaneous transluminal coronary angioplasty (PTCA) is inflated and forced into contact with the plaque, the balloon can have a tendency to move or slip longitudinally in relation to the lesion or the vessel wall being treated.

Cutting balloons (atherotomy) have recently shown clinical efficacy in preventing the reoccurrence of some types of restenosis (specifically calcified lesions and in-stent restenosis). The cutting balloon is a coronary dilatation catheter with 3 to 4 atherotomes (microsurgical blades) bonded longitudinally on the balloon surface. As the cutting balloon is inflated, the atherotomes move radially and open the occluded artery by incising and compressing the arterial plaque in a controlled manner. An additional advantage of the cutting balloon is that it maintains its position during inflation by using the metal blades on the external surface of the balloon to penetrate into the tissue and prevent the balloon from moving.

Accordingly, it is the principal objective of the present invention to provide a PTA or PTCA balloon that, like a cutting balloon, has a reduced potential of slippage when inflated in a vessel.

DESCRIPTION

Figure 1:
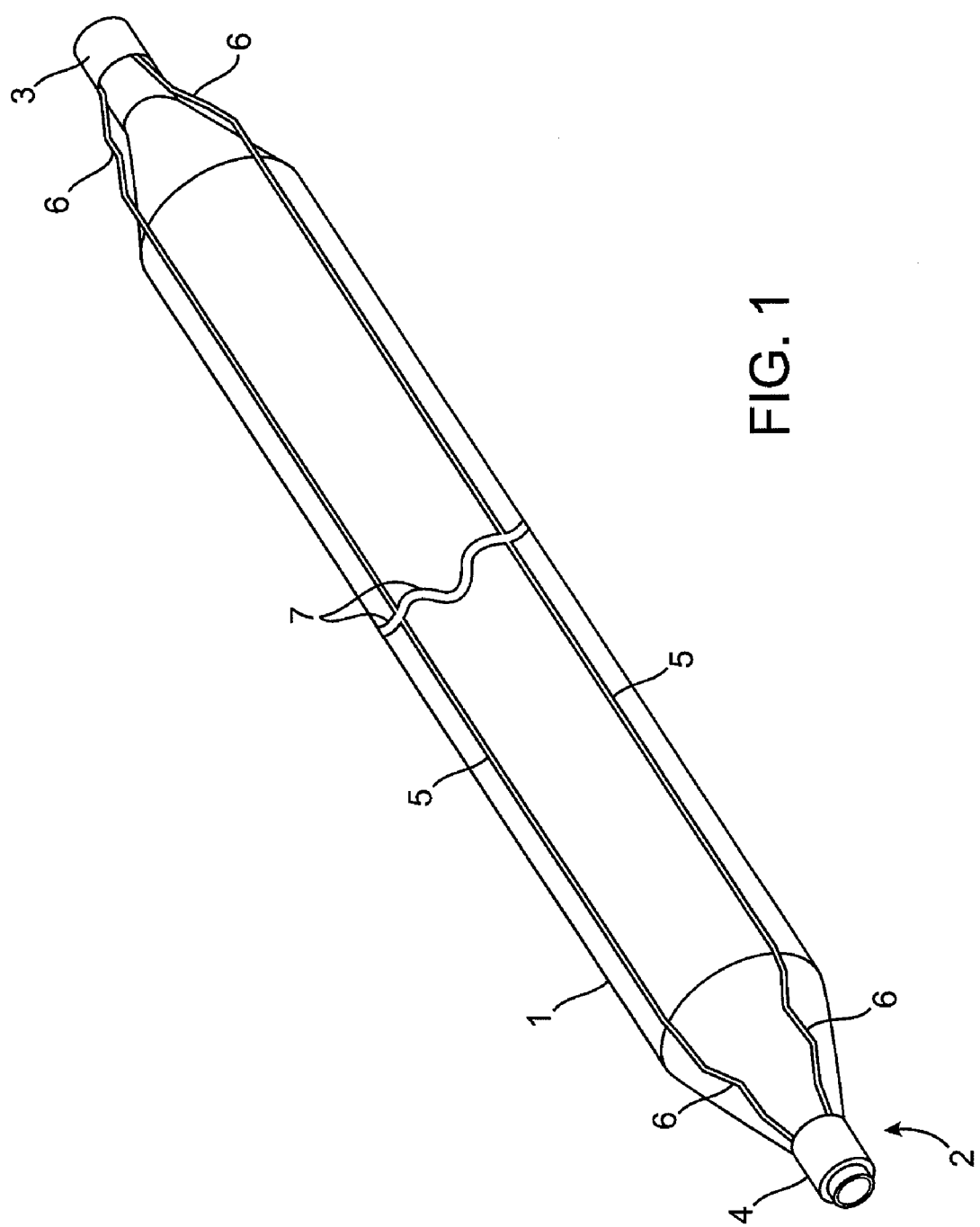
FIG. 1 is a perspective view of an inflated angioplasty balloon incorporating a non-deployable stent according to the present invention.
Figure 2:
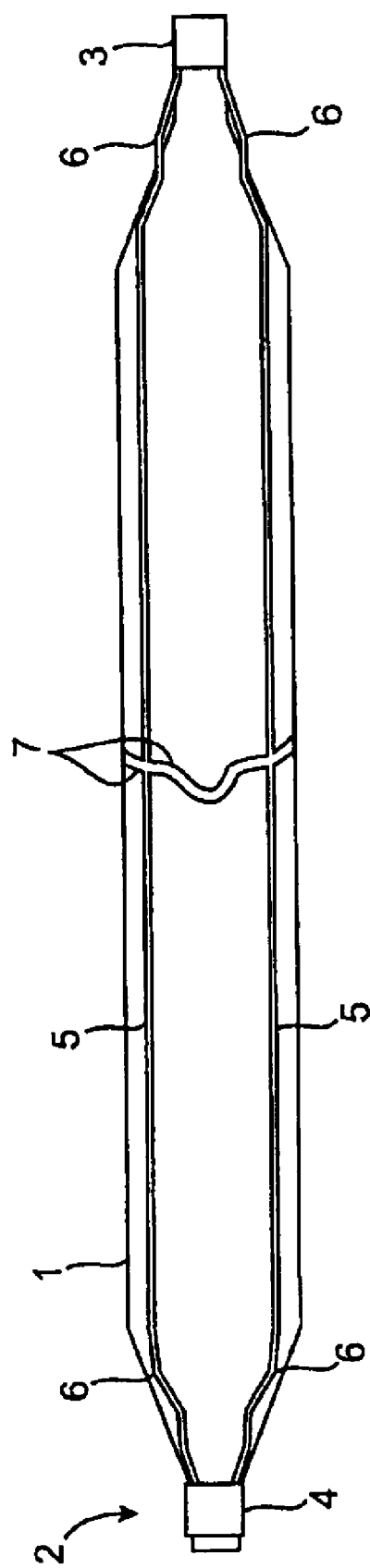
FIG. 2 is a plan view of the inflated angioplasty balloon and non-deployable stent of FIG. 1.

The non-deployable stent of the present invention may be used in conjunction with a conventional balloon catheter. A PTA or PTCA catheter (dilatation catheter) may be a coaxial catheter with inner and outer members comprising a guide wire lumen and a balloon inflation lumen, respectively. Each member can have up to 3 layers and can be reinforced with braids. The proximal end of the catheter has a luer hub for connecting an inflation means, and a strain relief tube extends distally a short distance from the luer hub. The distal ends of the outer and inner members may include a taper. The catheter shaft is built using conventional materials and processes. A catheter having multi-durometer tubing with variable stiffness technology is also a possibility. The catheter should be compatible with a 6 F guide catheter. Optionally, the catheter may be a multi-lumen design.

The balloon 1 may be made of either nylon or nylon copolymer (compliant, non-puncture) or PET (high pressure, non-compliant) with a urethane coating to provide tackiness. The balloon may be a multi-layered balloon with a non-compliant inner layer to a most compliant outer layer. For example, a inner most layer of PET, which provides a higher pressure balloon, surrounded by an outer layer of nylon, which provides a more puncture-resistant surface. The balloon may be from 1.5-12 mm in diameter (1.5-4 mm for coronary and 4-12 mm for peripheral vessels) and 15-60 mm in length (15-40 mm for coronary and up to 60 mm for peripheral vessels). The balloon inflation pressure will be from 8-20 atmospheres, depending on the wall thickness of the balloon. When inflated, the balloon ends or necks are cone-shaped.

In keeping with the invention, the balloon is provided with a Nitinol (NiTi) structure, generally designated 2, that incorporates bends for both radial and longitudinal expansion of the Nitinol structure 2 in response to longitudinal and radial expansion of the balloon during inflation, so that the Nitinol structure 2 maintains the balloon in its intended position during inflation. This Nitinol structure 2 can be described as a non-deployable or temporary stent that provides for both controlled cracking of vessel occlusion and gripping of vessel wall during an angioplasty procedure. The Nitonol structure 2 comprises a laser cut hypo tube that expands upon inflation of the balloon, but collapses upon deflation of the balloon because of the super-elastic properties of the Nitinol material, rather than remain expanded in the deployed condition, as would stents in general.

The Nitinol structure or non-deployable stent 2 has a proximal end 3, a distal end 4, and, therebetween, anywhere from 3-12 struts or wires 5 (depending on balloon size—but most likely 3-4 struts) with a pattern of radial and longitudinal bends. The use of laser cutting in connection with stent manufacture is well known (See, e.g., Meridan et al. U.S. Pat. No. 5,994,667), as is the use of the super-elastic nickel—titanium alloy Nitinol (see e.g., Huang et al. U.S. Pat. No. 6,312,459).

As seen in FIGS. 1-4, each end of the linear, longitudinally aligned four struts 5 has a sinusoidal bend 6 that allows the laser cut hypo tube to expand longitudinally when the balloon 1 is inflated. The linear length of the sinusoidal bends 6 is sized to accommodate the longitudinal expansion of the balloon 1 due to inflation. The strut or wire 5 cross sectional shape can be round, triangular or rectangular. Preferred diameter of the struts 5 ranges from 0.003 to 0.010 inch.

Figure 3:
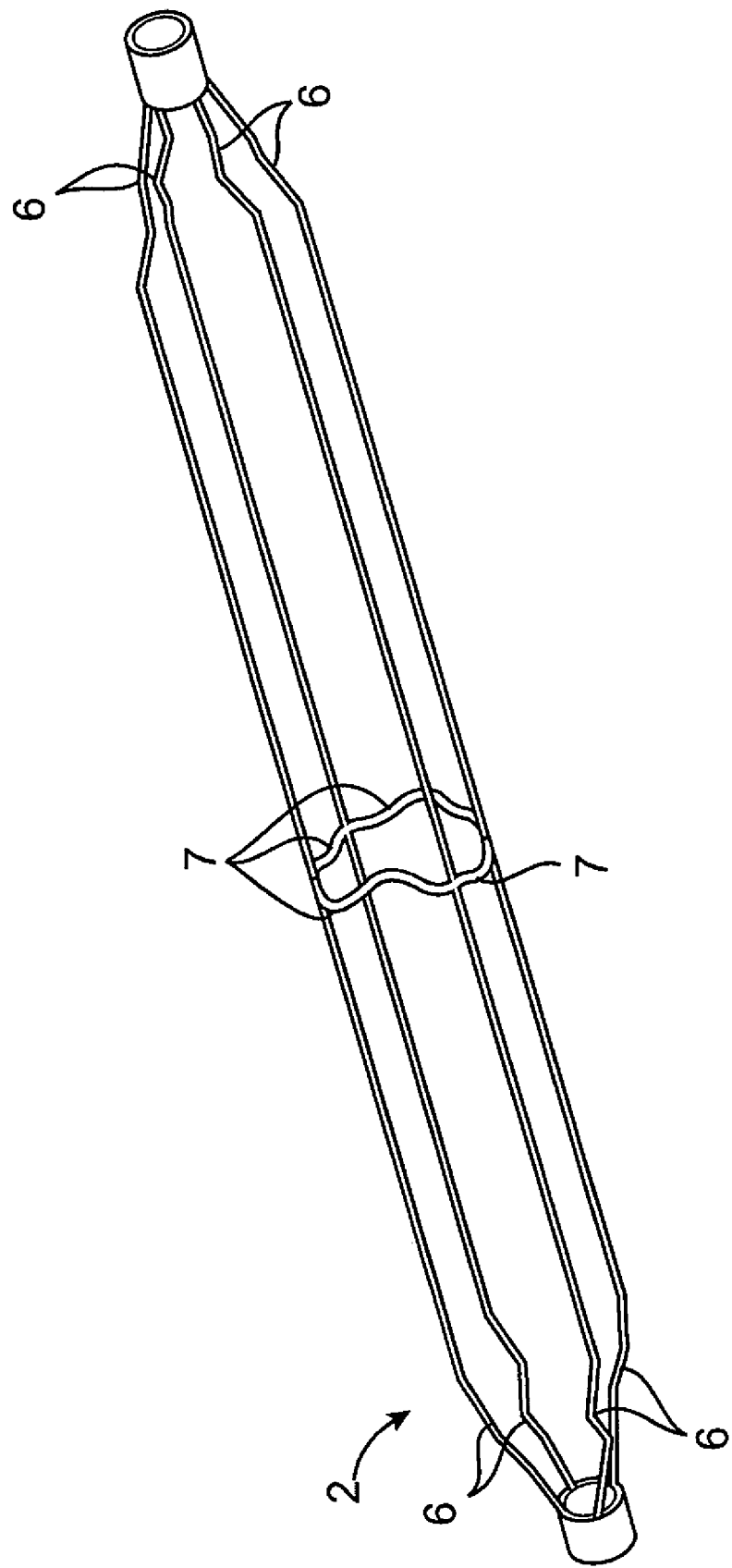
FIG. 3 is a perspective view of the non-deployable stent in its expanded condition, as shown in FIG. 1, with the angioplasty balloon removed so as to more clearly show the stent.
Figure 4:
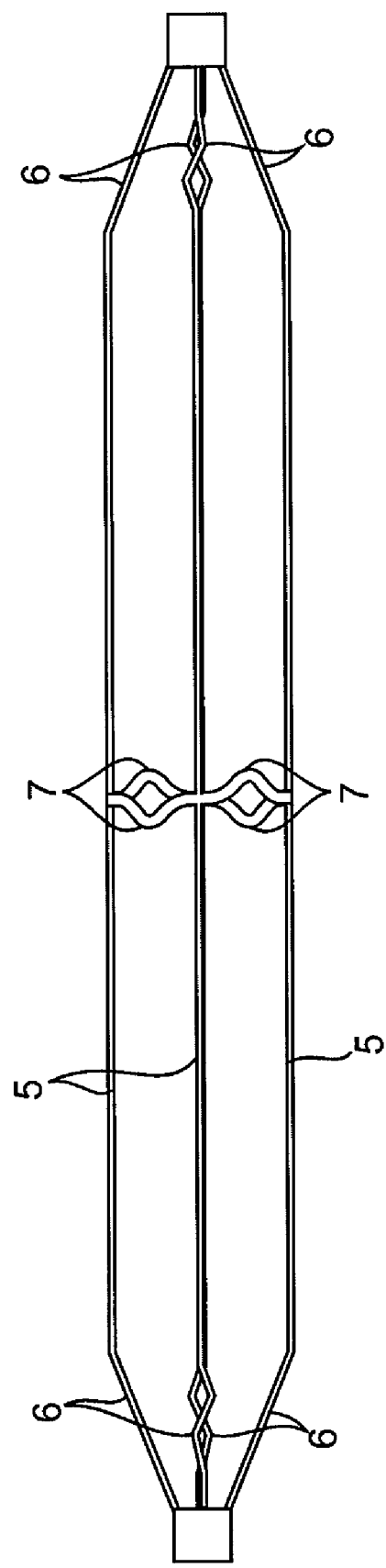
FIG. 4 is a plan view of the non-deployable stent of FIG. 3.
Figure 5:
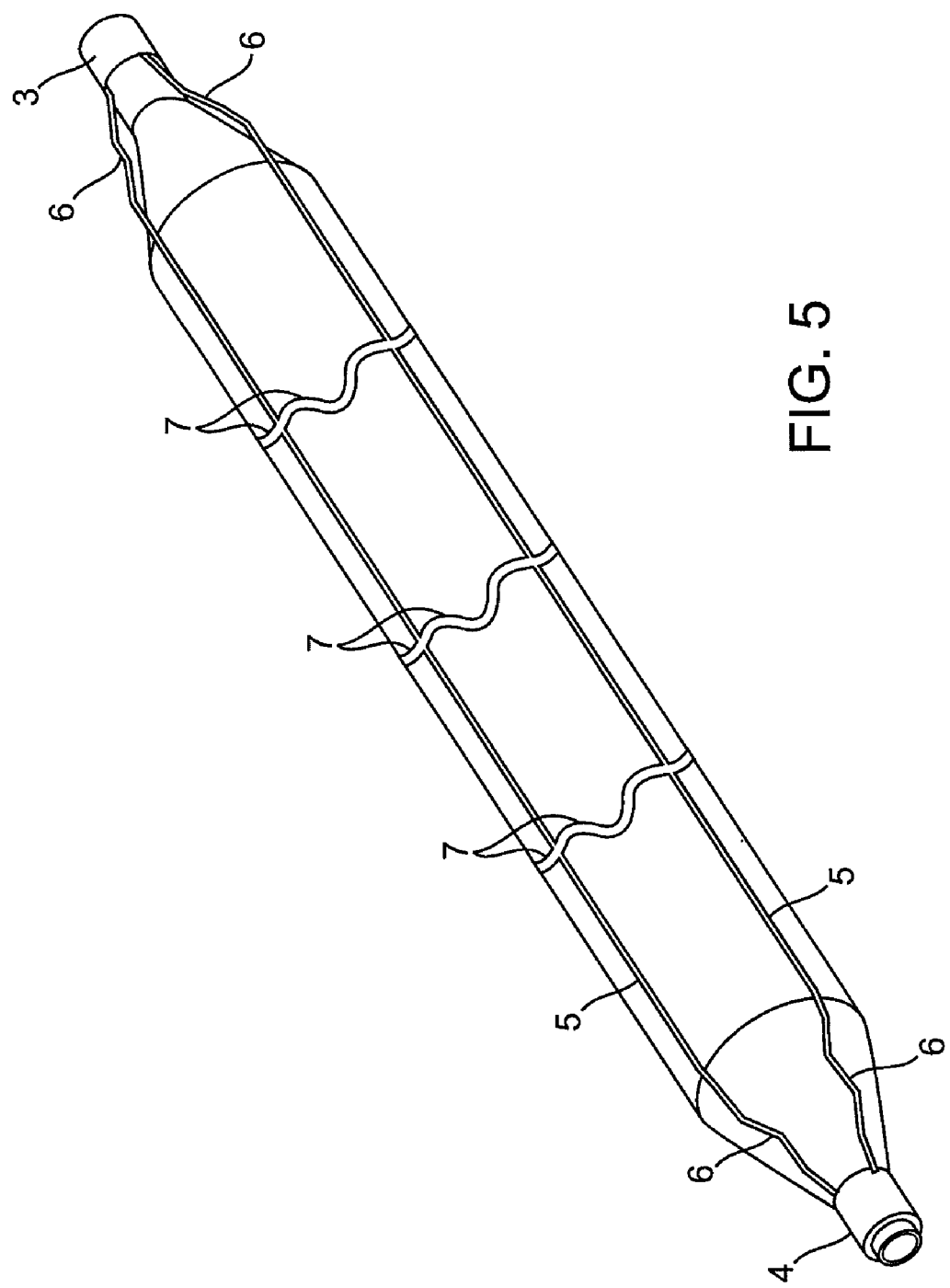
FIG. 5 is a perspective view of an alternate embodiment of the non-deployable stent associated with an angioplasty balloon that has a longer working length than the angioplasty balloon shown in FIGS. 1 and 2.

At the longitudinal center of the hypo tube, a U-shaped circumferential connector 7 joins each strut 5 to its adjacent strut. As best seen in FIGS. 3 and 4, the U-shaped connectors 7 are on opposing sides of the central radial axis. The distal end 4 of the hypo tube is adhered to the distal neck of the balloon or the distal end of the catheter shaft, and the proximal end 3 of the hypo tube is either attached to the proximal neck of the balloon or to the proximal end of the catheter shaft. The struts 5 may be attached to the working region of the balloon 1 to assist the hypo tube in staying with the balloon as it inflates and deflates, and an adhesive, such as a cyanoacrylate adhesive, may be used to tack the struts down onto balloon at various points.

Catheter shafts to which the balloon and laser cut hypo tube are attached can have diameters ranging from 2.5 F to 8 F, and the distal end may be tapered and slightly less in diameter than the proximal end.

Figure 6:
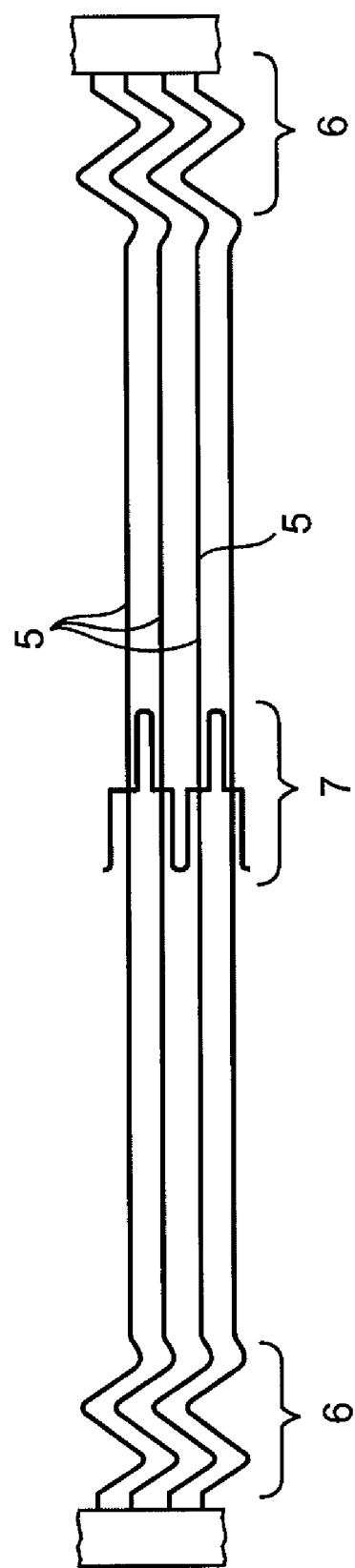
FIG. 6 is an engineering drawing showing, in plan view, the layout of a non-deployable stent adapted to be used with an angioplasty balloon of 20 mm in length. (All dimensions shown in the drawing are in inches.)

In FIG. 6, the dimensions of the laser cut hypo tube are for use with a 3 mm (0.118 in) diameter by 20 mm length balloon. The circumference of a 3 mm balloon is nD=3.14(3 mm)=9.42 mm or 0.37 in. As can be readily appreciated, the total length of all U-shaped connectors 7 (up and back) must be greater than the circumference of the inflated balloon 1. The length of each U-shaped connector 7 (up and back), may be calculated using the following equation:

$$\frac{\Pi d}{n},$$

where d is the diameter of the inflated balloon and n is the number of struts. The total length of the U-shaped bends (up and back) must exceed this length.

The resulting number is divided by 2 to get the length which each up-and-back side of the U-shaped connector should exceed. For example: for a 3 mm balloon compatible, laser-cut hypo tube with four struts, the length of each U-shaped connector (up and back) is 0.37 inch divided by 4=0.0925 in. Further divide by 2 and to get 0.04625 in. This is the length that each side of the U-shaped connector must exceed.

Figure 7:
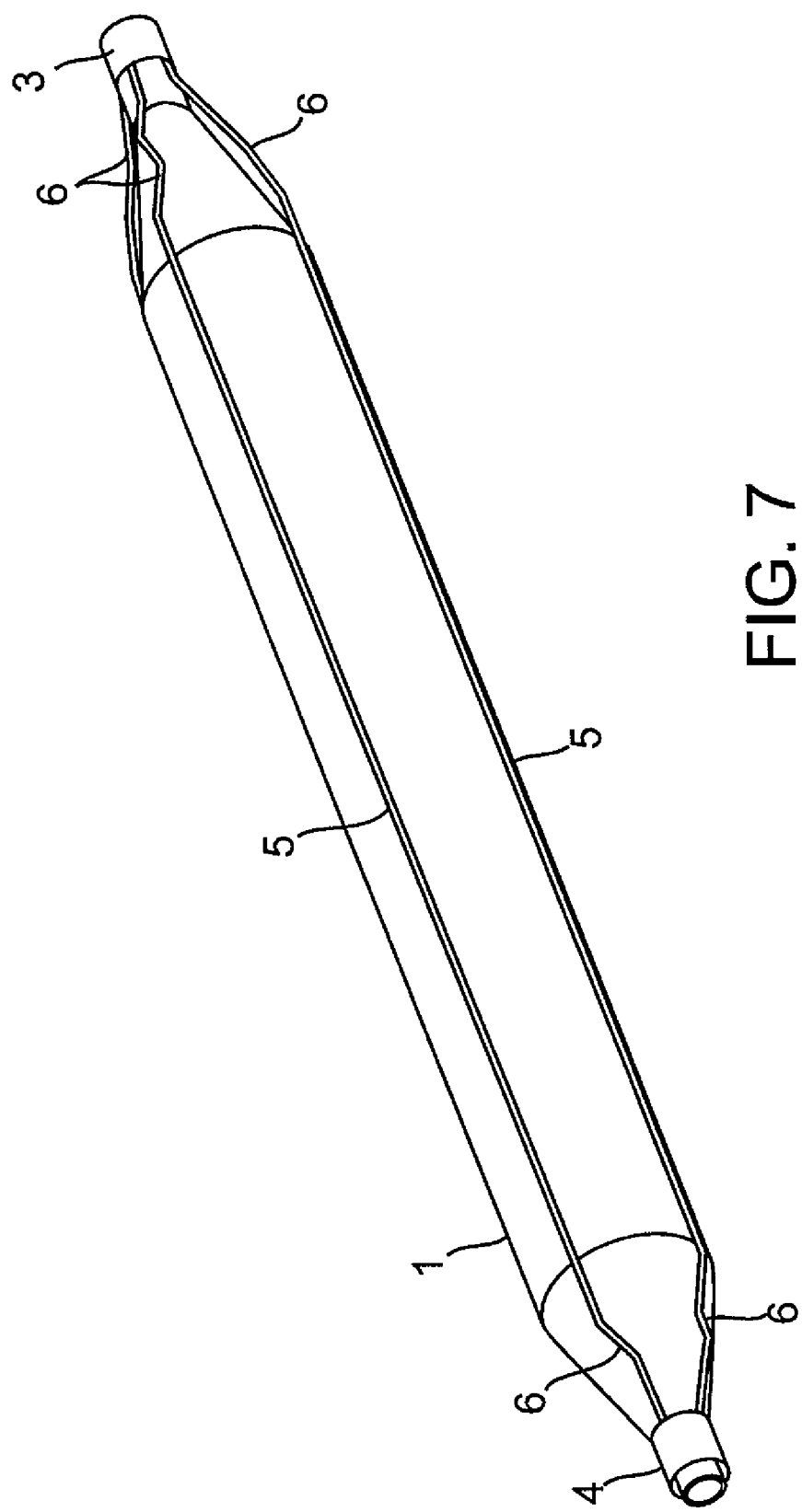
FIG. 7 is a perspective view of an inflated angioplasty balloon incorporating an alternative embodiment of a non-deployable stent which does not include any connecting elements between the struts intermediate the ends of the balloon.
Figure 8:
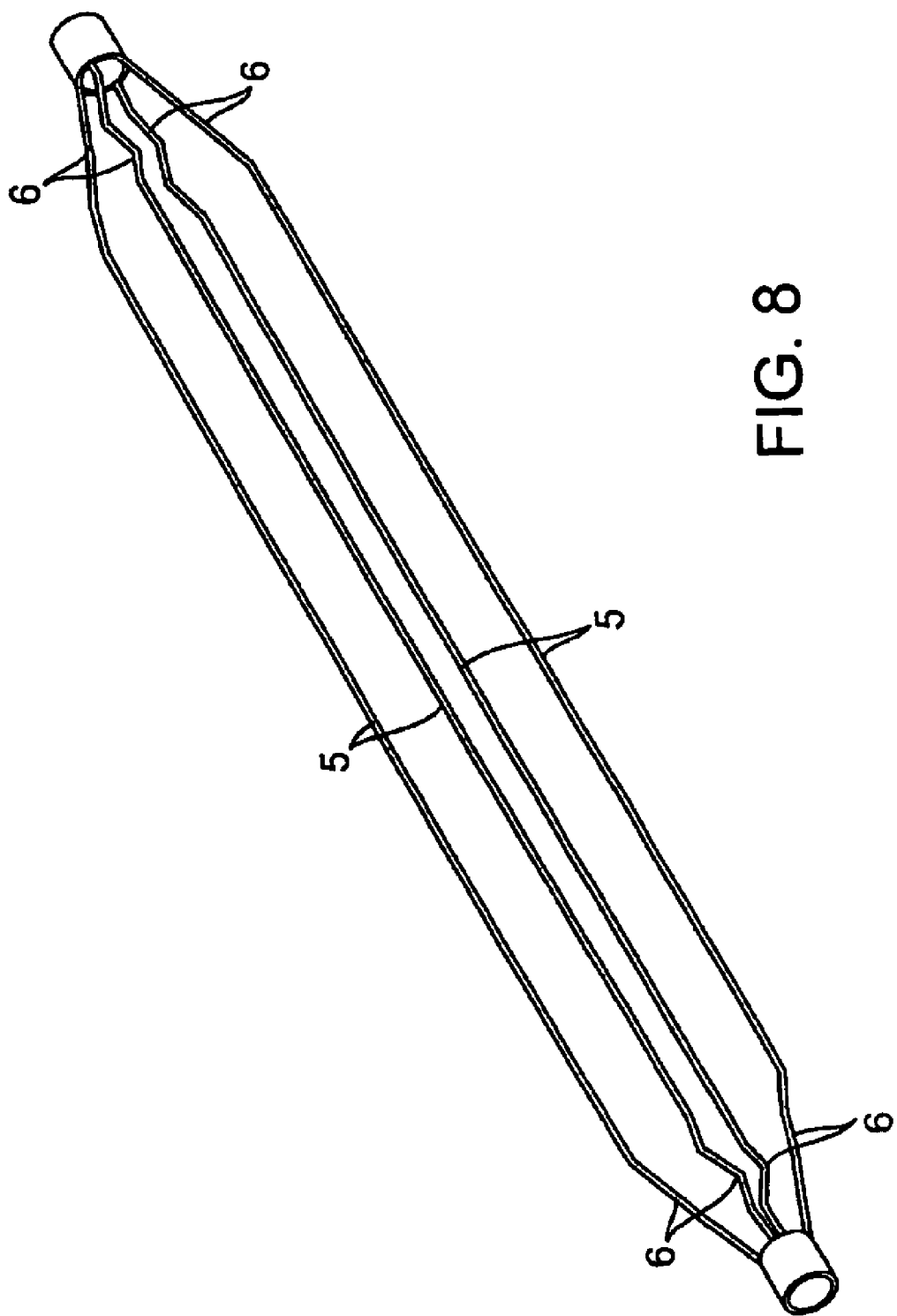
FIG. 8 is a perspective view of the non-deployable stent shown in FIG. 7, with the angioplasty balloon removed so as to more clearly show the stent.
Figure 9:
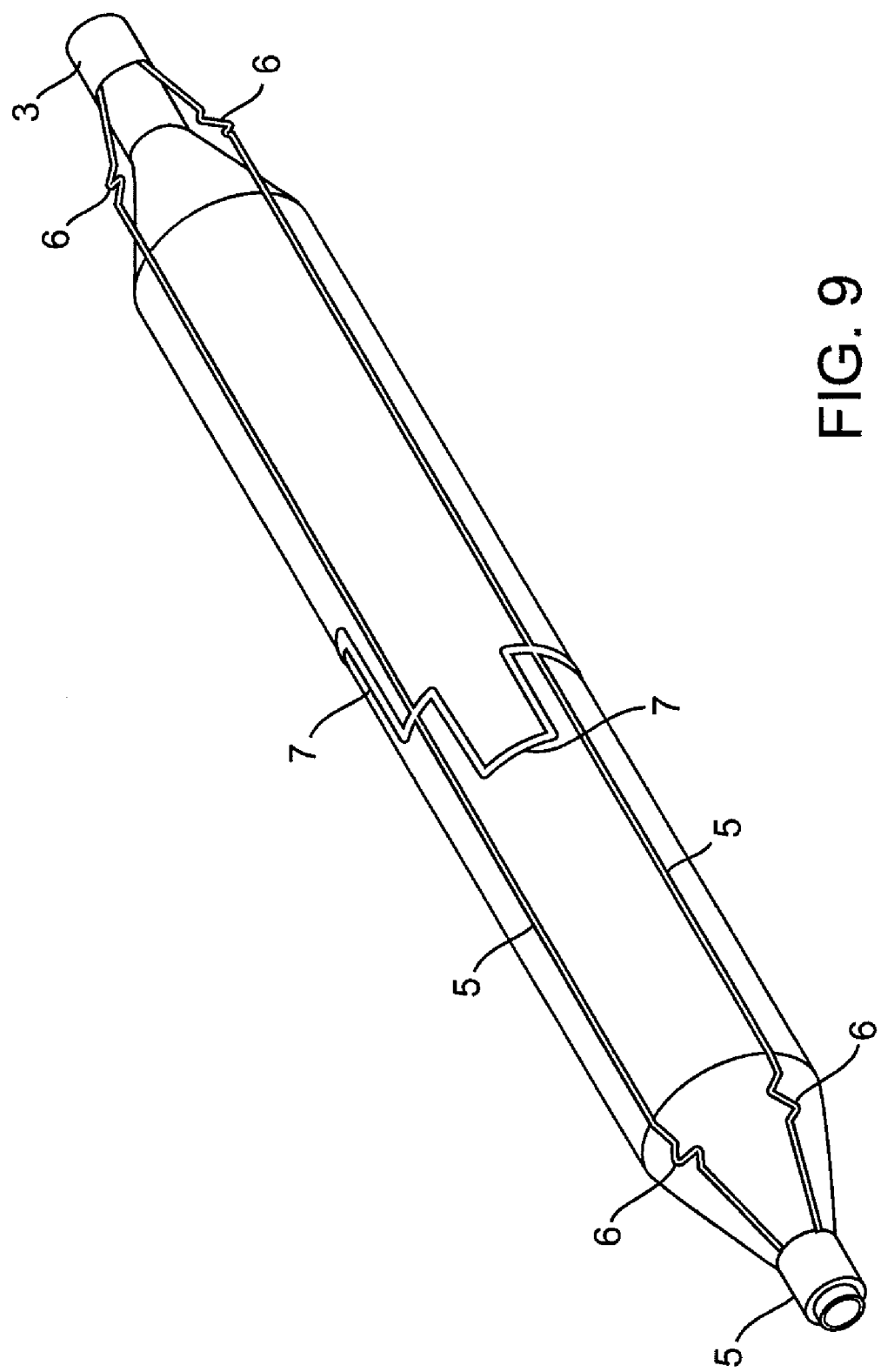
FIGS. 9 and 10 are perspective views similar to FIGS. 1, 5, and 7 showing a further embodiment of the invention.
Figure 10:
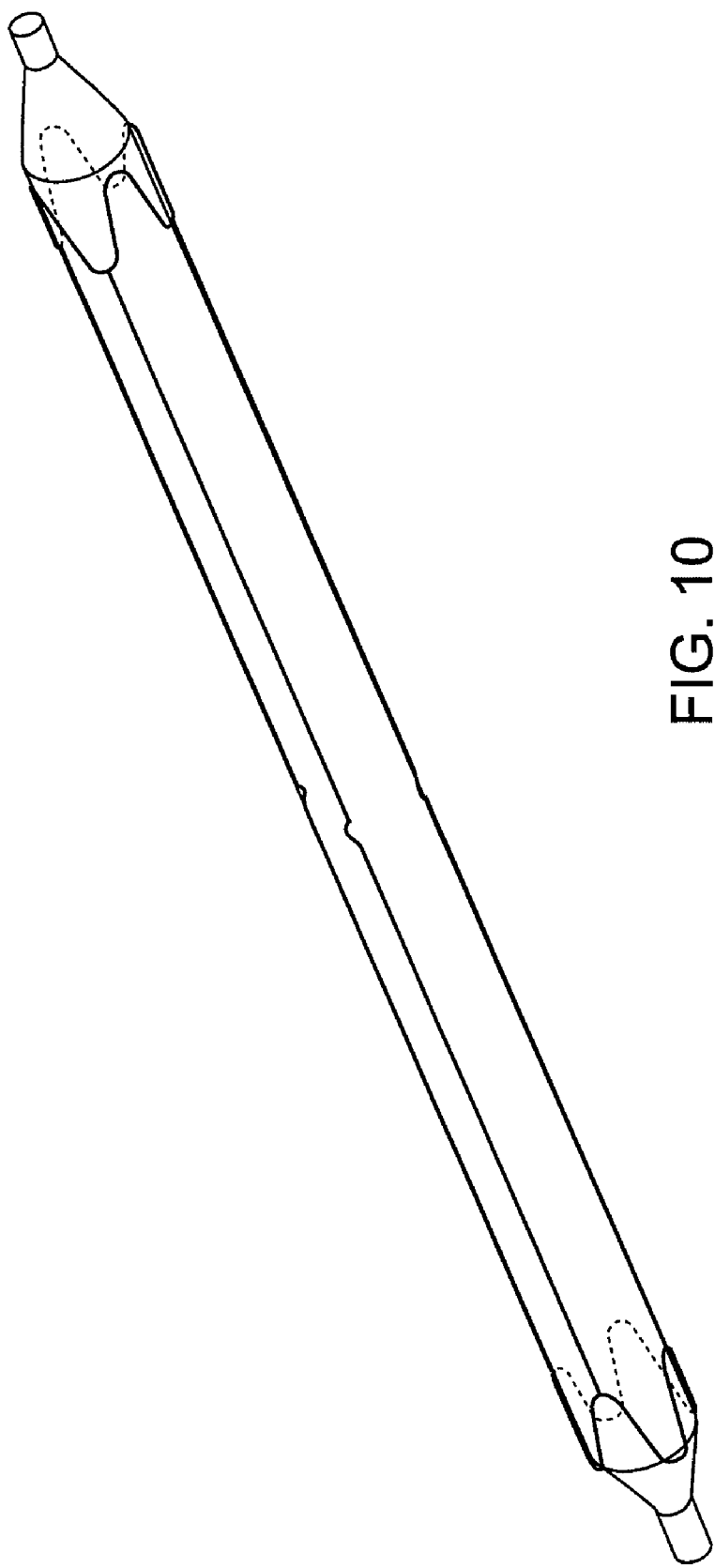
Figure 11:
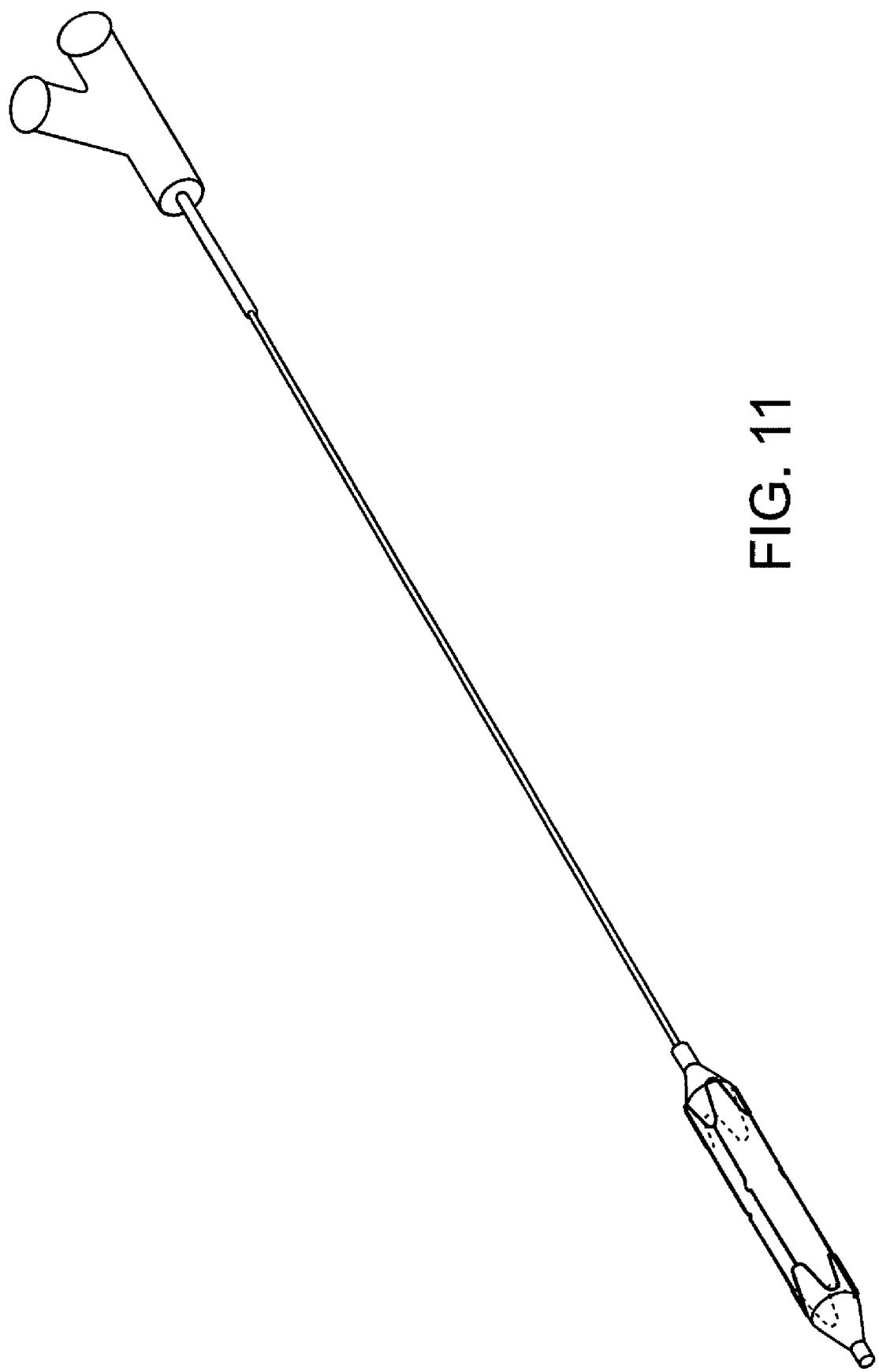
FIG. 11 is a perspective view of a further embodiment of the present invention showing the balloon and non-deployable stent in conjunction with a catheter.

There is also one or more sets of U-shaped connectors 7 in between the sinusoidal bends 6. The set includes one U-shaped connector for each strut (3 struts—a set of 3 U-shaped connectors; 4 struts—a set of 4 U-shaped connector; and so on). The number of U-shaped connector sets depends on the length of the balloon and thus, the length of the laser cut hypo tube. For a 20 mm length balloon, there is one set of U-shaped connectors spaced 10 mm from the end (at the halfway point along length of balloon). For a 40 mm length balloon, there are three sets of U-shaped connectors spaced in 10 mm increments (the first set is spaced 10 mm from one end; the second set is spaced 10 mm from first set; and the third set is spaced 10 mm from each the second set and the other end). The equation for number of sets of U-shaped connectors.

$$\frac{L}{10} - 1,$$

where L=length of balloon in mm. Other embodiments, such as those shown in FIGS. 7 and 8, have linear, longitudinally aligned struts 5 with bends 6 at each end which do not incorporate the intermediate U-shaped connectors.

What is claimed:

1. An angioplasty balloon catheter comprising:
   a catheter shaft carrying an inflatable/deflatable balloon having a proximal end and a distal end; and
   a non-deployable radially expansible stent comprising a hypo tube disposed over the balloon and comprising a proximal end; a distal end; and at least three longitudinally aligned, radially-spaced struts, wherein each strut extends from the proximal end to the distal end and prior to radial expansion has one or more bends that allow longitudinal expansion of the strut to accommodate radial expansion of the stent upon inflation of the balloon; wherein the distal end of the hypo tube is attached to the distal end of the catheter shaft and the proximal end of the tube is attached to the proximal end of the catheter shaft and the stent is made of a material having a memory so that the stent radially collapses and the struts longitudinally shorten upon deflation of the balloon.

2. The angioplasty balloon of claim 1 wherein the stent is made of an alloy of nickel and titanium.

3. The angioplasty balloon of claim 1 wherein the struts of the stent have a diameter of from 0.003" to 0.010".

4. The angioplasty balloon of claim 1 wherein the bends in the struts of the stent are sinusoidal.

5. The angioplasty balloon of claim 1 wherein the hypo tube is laser cut.

6. The angioplasty balloon of claim 1 wherein the stent is secured to the balloon by an adhesive.

7. The angioplasty balloon of claim 6 wherein the adhesive is a cyanoacrylate.

8. The angioplasty balloon of claim 1 wherein the struts of the stent are connected to each other intermediate the proximal end and distal end by connectors that include a bend which allows longitudinal expansion of the connectors to accommodate radial expansion of the balloon.

9. The stent of claim 8 wherein the connectors in the struts comprise sinusoidal bends.

* * * * *